US006159164A

United States Patent [19]
Neese et al.

[11] Patent Number: 6,159,164
[45] Date of Patent: *Dec. 12, 2000

[54] BLOOD SAMPLING SYSTEM

[75] Inventors: Jon Neese; Ben D. Shirley, both of Salt Lake City, Utah

[73] Assignee: Utah Medical Products, Midvale, Utah

[ * ] Notice: This patent is subject to a terminal disclaimer.

[21] Appl. No.: 09/060,925

[22] Filed: Apr. 15, 1998

Related U.S. Application Data

[63] Continuation of application No. 08/560,832, Nov. 20, 1995, Pat. No. 5,759,160.

[51] Int. Cl.$^7$ .................................................. A61B 5/00
[52] U.S. Cl. .................................... 600/578; 600/573
[58] Field of Search ................................... 600/573, 578, 600/579

[56] References Cited

U.S. PATENT DOCUMENTS

| | | |
|---|---|---|
| 986,263 | 3/1911 | Bevill . |
| 2,357,238 | 3/1944 | Trimble . |

(List continued on next page.)

FOREIGN PATENT DOCUMENTS

| | | |
|---|---|---|
| 0 208 975 | 6/1986 | European Pat. Off. . |
| 0575916A2 | 6/1993 | European Pat. Off. . |
| 0575917 A2 | 6/1993 | European Pat. Off. . |

OTHER PUBLICATIONS

Implantable Vascular Access Devices, Winters, Vina, Oncology Nursing Forum 11 No. 6, Nov./Dec. 1984.
Prospective randomized evaluation of two methods of drawing coagulation studies from haparinized arterial lines, Cannon, Kerry etal. Clinical Investigations in Critical Care, Jul. 1985, vol. 14, No. 4, pp 392–95.

Phlebotomy for Diagnostic Laboratory Tests in Adults, Smoller, Bruce et al. The New England Journal of Medicine, May 8, 1986, vol. 314, No. 19, pp 1233–1236.

(List continued on next page.)

*Primary Examiner*—Max Hindenburg
*Assistant Examiner*—Pamela Wingood
*Attorney, Agent, or Firm*—Clayton, Howarth & Cannon, P.C.

[57] ABSTRACT

An apparatus for sampling blood through an intravenous or intraarterial tube which does not interfere with normal operation of an infusion operation or a direct pressure monitoring operation. A needleless sampling site at which fluid can be removed is connected to the tube. A chamber is provided which is connected to the tube such that fluid can be interchanged between the tube and the chamber. A plunger is provided for drawing the fluid from the tube into the chamber and for expelling the fluid from the chamber into the tube. In its normal position, the plunger blocks the interconnection between the tube and the chamber. When in its sampling position, the plunger creates a vacuum in the chamber causing the fluid in the tube to be aspirated into the chamber. The aspirating action causes fluid in the patient to be drawn up to the sampling site. An actuator, which can be operated by a single hand of a medical practitioner, imparts an appropriate feel to the system operation. A practitioner can carefully control the aspiration and expulsion operations of the system due to the resistance provided against the practitioner's hand movements and configuration of the body and the actuator means. The movement of the plunger is such that fluid is selectively drawn into and expelled from the chamber.

34 Claims, 7 Drawing Sheets

U.S. PATENT DOCUMENTS

| | | |
|---|---|---|
| 2,847,996 | 8/1958 | Cohen et al. . |
| 3,291,151 | 12/1966 | Loken . |
| 3,344,785 | 10/1967 | Hamilton . |
| 4,013,064 | 3/1977 | Patel et al. . |
| 4,051,852 | 10/1977 | Villari . |
| 4,105,500 | 8/1978 | Libman et al. . |
| 4,114,617 | 9/1978 | Turner et al. . |
| 4,214,779 | 7/1980 | Losell . |
| 4,219,021 | 8/1980 | Fink . |
| 4,263,922 | 4/1981 | White . |
| 4,289,648 | 9/1981 | Hoskins et al. . |
| 4,316,473 | 2/1982 | Beskin . |
| 4,335,717 | 6/1982 | Bujan et al. . |
| 4,341,224 | 7/1982 | Stevens . |
| 4,364,383 | 12/1982 | Vcelka . |
| 4,370,987 | 2/1983 | Bazell et al. . |
| 4,385,637 | 5/1983 | Akhavl . |
| 4,457,753 | 7/1984 | Pantrone . |
| 4,533,348 | 8/1985 | Wolfe et al. . |
| 4,634,427 | 1/1987 | Hannula et al. . |
| 4,673,386 | 6/1987 | Gordon . |
| 4,763,648 | 8/1988 | Wyatt . |
| 4,796,644 | 1/1989 | Polaschegg . |
| 4,838,855 | 6/1989 | Lynn . |
| 5,374,401 | 12/1994 | von Berg . |
| 5,759,160 | 6/1998 | Neese et al. ............................ 600/573 |

OTHER PUBLICATIONS

Medical Vampires, Burnum, John F. The New England Journal of Medicine, May 8, 1986, vol. 314, No. 19, pp 1250–1251.

Stopcock: Bacterial contamination in invasive monitoring systems, Walrath, Jo Marie et al. Heart & Lung, Jan.–Feb. 1979, vol. 8, No. 1, pp 100–04.

Stopcock Contamination in an ICU, McArthur, Barbara J. et al. American Journal of Nursing, Jan. 1975, pp 96–97.

Errors in Intraoperative Hematocrit Determination, Bourke, Denis L. Anesthesiology, vol. 15, No. 3, Sep. 1976, pp 357–359.

Effect of sample dilutions on arterial blood gas determinations, Dennis, Richard C. et al. Critical Care Medicine, Dec. 1985. Pp., 1067–1068.

BLOOD SAMPLING SYSTEM

This application is a continuation of application Ser. No. 08/560,832 filed Nov. 20, 1995 U.S. Pat. No. 5,759,160.

BACKGROUND

1. The Field of the Invention

This invention relates to medical devices used to repeatedly obtain blood samples from a patient by way of an indwelling infusion line.

2. The Background Art

In many cases, the condition of a patient requires that an intravenous/intraarterial tube or catheter be inserted into a blood vessel. The patient's blood vessel is connected by the tube to a source of fluid which provides fluid such as a medicament, and which is also connected to a pressure transducer which senses the pressure within the patient's blood vessel.

In critical care situations, it is necessary to periodically obtain samples of the patient's blood. Importantly, each procedure carried out using a needle stick increases the likelihood of a health care worker being inadvertently stuck and thereby being infected from a contaminated needle. Rather than stick a patient with a needle each time blood must be drawn, it is preferred that blood be drawn through the tube already connected to the patient's blood vessel. Since the tube connected to the patient's blood vessel contains fluid other than blood, such as saline solution and some medication, it is necessary to draw the patient's blood up into the tube so that a blood sample can be obtained which is substantially unadulterated by the fluid which is being supplied to the tube by an external source. Once substantially unadulterated blood has been drawn up the tube to a sampling site, the blood sample can be collected into a sample container.

Several devices have been proposed to draw blood up the tube connected to a patient's blood vessel to a sampling site. All of the proposed devices utilize a vacuum creating structure in communication with the tube to draw blood out of the patient's blood vessel up to, and past, a sampling site on the tube. Disadvantageously, many of the previously available devices require two-handed operation by a medical practitioner. Some of the previous devices utilize a conventional medical syringe to create the suction necessary to draw the blood up the tube. Such syringes are often unwieldy to use and their typical long, narrow dimensions makes them cumbersome. Many of the previously available devices are complicated and expensive. Moreover, some of the previously available devices include sharp bends in the fluid path and/or relatively long supplementary fluid paths both of which result in residual blood and fluid remaining in the fluid path which can cause problems such as clotting.

In view of the forgoing, it would be an advance in the art to provide a blood sampling system which overcomes the difficulties and disadvantages present in the previously available devices.

BRIEF SUMMARY AND OBJECTS OF THE INVENTION

In view of the above described state of the art, the present invention seeks to realize the following objects and advantages.

It is a primary object of the present invention to provide a patient fluid sampling system which is compact and convenient to operate.

It is also an object of the present invention to provide a blood sampling system in communication with a patient's blood vessel which can aspirate blood up to a sampling site with the medical practitioner using not more than one hand.

It is also an object of the present invention to provide an in-line blood sampling system which is reliable and inexpensive to manufacture.

It is a further object of the present invention which minimizes the risk of infection due to operation thereof.

It is a further object of the present invention to provide a blood sampling system which provides appropriate resistance and sensation for the medical practitioner using the system.

These and other objects and advantages of the invention will become more fully apparent from the description and claims which follow, or may be learned by the practice of the invention.

The present invention provides a system and method for sampling a body fluid through an infusion tube attached to a patient's body. The system is particularly adapted for use with a tube which is connected to a patient, such as patient's blood vessel, which is infusing a fluid into the vessel, for example from an infusion device and/or which is connected to a pressure transducer. When a blood sample is not being obtained, the sampling system allows an infusion operation and/or a direct pressure monitoring operation to be carried on unaffected.

The preferred embodiments of the present invention include a sampling site connected to the tube at which fluid can be removed from the tube. The preferred sampling site is a needleless sampling site. A chamber, or means for forming a chamber, is provided. The chamber is preferably formed within a body fabricated from a clear plastic material suitable for medical applications. The tube connected to the patient has access to the chamber via a means for connecting the chamber to the tube such that fluid can be interchanged between the tube and the chamber.

A plunger or plunger means is also provided. The plunger functions to alter the size of the chamber so that fluid is drawn from the tube into the chamber and also the fluid is expelled from the chamber into the tube. In some preferred embodiments, a means for actuating the plunger means is also provided. In its normal position, the plunger minimizes the size of the chamber. When actuated to a sampling position, the plunger creates a vacuum in the chamber causing any fluid in the tube to be aspirated into the chamber. The aspiration action causes fluid in the patient to be drawn up into a sampling site. The plunger is provided with a resilient tip which slidably engages the side of the chamber.

The apparatus desirably provides operating characteristics which impart an appropriate feel to the system is when it is handled and used by a medical practitioner. A medical practitioner can operate the aspiration and expulsion features of the system with only a single hand, if desired.

Moreover, a medical practitioner can carefully control the aspiration and expulsion operations of the system due to the resistance provided against the practitioner's hand movements and the configuration of the apparatus.

Advantageously, in one preferred embodiment of the inventions a perpendicularly to the chamber, passes through the apparatus body, and includes a means for receiving a portion of a user's hand. The actuator extends outwardly from the chamber only a short distance. A means is provided for translating the force applied by the user's hand in a direction substantially perpendicular to the chamber into movement of the plunger means such that fluid is selectively drawn into and expelled from the chamber. In other embodiments of the invention the plunger and the body are positioned within a housing so that as the body and the plunger cooperate to increase or decrease the size of the chamber while the overall length of the apparatus remains within the length of the housing.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference will now be made to the drawings wherein like structures will be provided with like reference designations.

Figure 1:
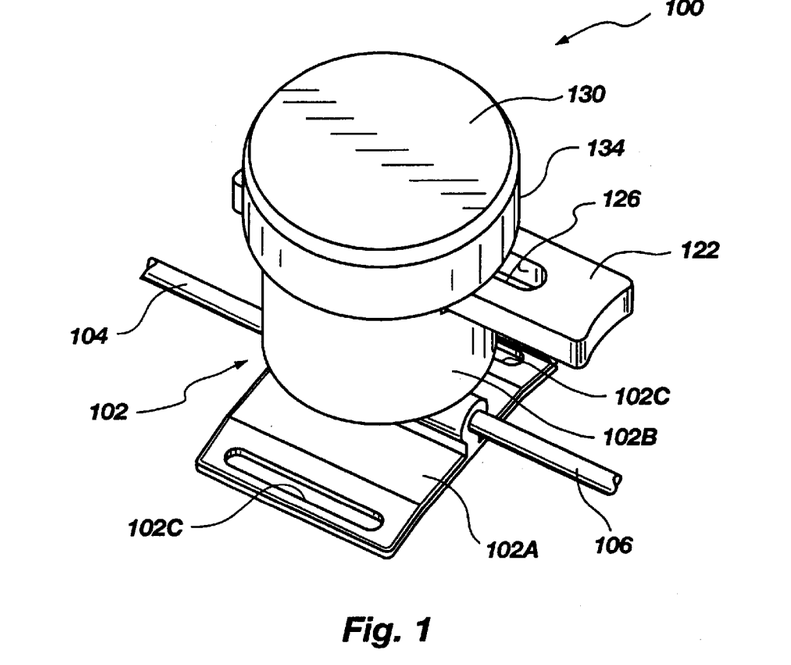
FIG. 1 is a perspective view of a first presently preferred embodiment of the present invention.

Reference will first be made to FIG. 1 which is a perspective view of a first presently preferred embodiment of the present invention. The blood sampling system illustrated in FIG. 1, generally indicated at 100, is preferably placed in-line with a catheter used for pressure sensing or in-line with an intravenous infusion device. The blood sampling system 100 can be connected to other medical devices as known in the art and as explained herein. While the structures of the present invention are particularly adapted for use with sampling blood, it will be appreciated that the present invention can be used to sample other fluids, particularly biological fluids which are found in a patient's circulatory system, and this is to be understood whenever the term "blood" is used herein.

The blood sampling system 100 comprises a body, generally indicated at 102, which includes a base 102A having two slots 102C used for securing the base 102A to another object. For example, the base 102A may receive a strap (not illustrated) which wraps around an adjacent object, such as a pole or a patient's arm.

A chamber housing 102B is also part of the body 102. The base 102A and the chamber housing 102B are preferably fabricated as a single injection molded piece using a clear plastic material as known in the industry. All of the described components of the blood sampling system 100 are preferably fabricated from clear materials so that any bubbles present in the fluid can be observed. Desirably, the structure of the blood sampling system 100 of the present invention minimizes the creation of bubbles. A tube 104 leads to the patient (usually to an indwelling patient catheter represented in FIG. 5 at PC) and to a blood sampling site (represented generally at 156 in FIG. 5) at which blood will be collected. A tube 106 leads to a source of fluid (FS in FIG. 5) and to a pressure transducer (PT in the FIG. 5). A cap 130 is provided on the top of the body 102.

Figure 2:
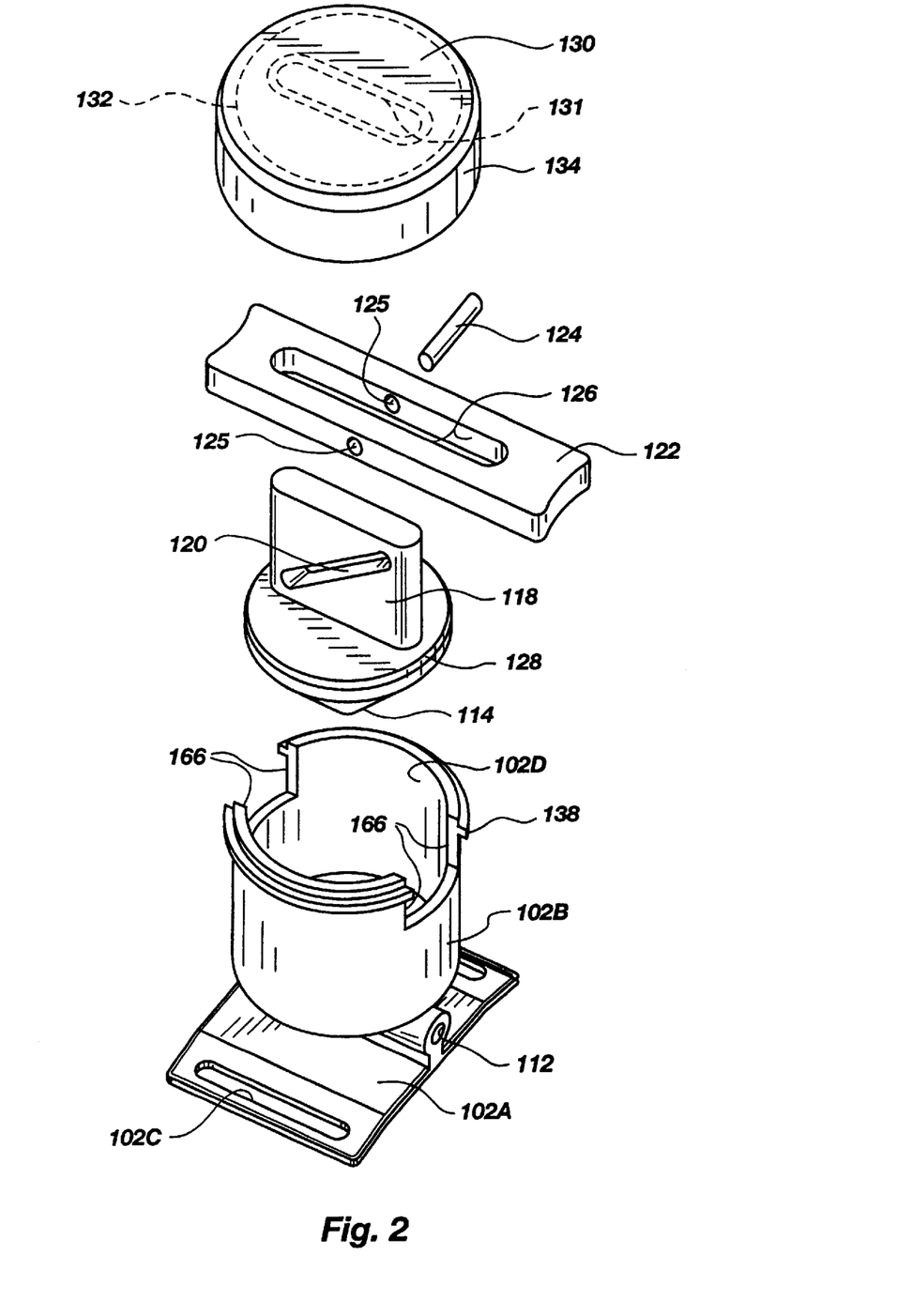
FIG. 2 is an exploded perspective view of the embodiment illustrated in FIG. 1.

Reference will now also be made to FIG. 2 which is an exploded perspective view of the embodiment illustrated in FIG. 1. As can be seen in FIG. 2, two openings 166 are provided in the wall of the body 102. An actuator 122 is configured to slidably rest within the openings 166 so that the actuator 122 passes through the body 102 (as also illustrated in FIG. 1). The actuator 122 is provided with an actuator slot 126.

Figure 3:
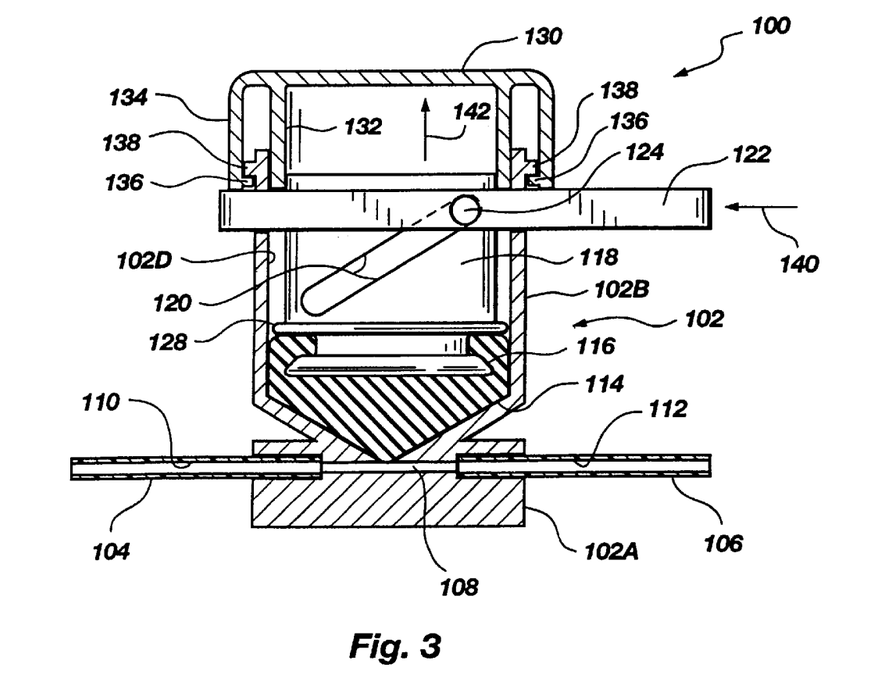
FIG. 3 is an elevational cross sectional view of the embodiment illustrated in FIG. 1 in a first operational position.

As shown best in FIG. 3, a plunger 128 is disposed within the body 102. The plunger 128 is generally cylindrical and is sized to substantially match the inner diameter of the body 102. A tip 114 is provided on the plunger 128. The tip 114 is preferably fabricated from a resilient material as is available in the art.

A fin 118 is provided on the upper side of the plunger 128. An inclined slot 120 is provided in the fin 118. A fin guide, shown in the cutaway portion of FIG. 2 at 131, is formed on the underside of the cap 130. The fin guide 131 is configured to receive the fin 118 therein as the fin 118 moves as will be explained shortly. The thickness of the fin 118 is preferably selected so that it closely fits within the actuator slot 126. When the blood sampling system 100 is assembled, the fin 118 is held captive within the actuator slot 126 and a rod 124 is placed through bores 125 provided in the actuator 122 and through the inclined slot 120. The rod 124 is preferably cylindrically shaped and is held in place in the bores 125 so that the rod 124 can slide along the inclined slot 120 to cause the movement of the plunger 128 within the body 102. It will be appreciated that the described structures are to be fabricated such that they withstand the pressures which will be encountered during use.

As will be explained further shortly, the actuator 122 and the body 102 together provide a structure which is comfortable, convenient, and efficient for a medical practitioner to operate for drawing blood up the tube 104 (FIG. 1) when desired to collect a blood sample. When it is desired to operate the blood sampling system 100, the medical practitioner pushes against the end of the actuator, most desirably with a thumb, finger, or palm of the hand, while also grasping the body 102 and/or the cap 130 with one or more fingers of the same hand. This advantageously allows efficient one-handed operation of the blood sampling system 100 in a manner not possible prior to the present invention.

Figure 4:
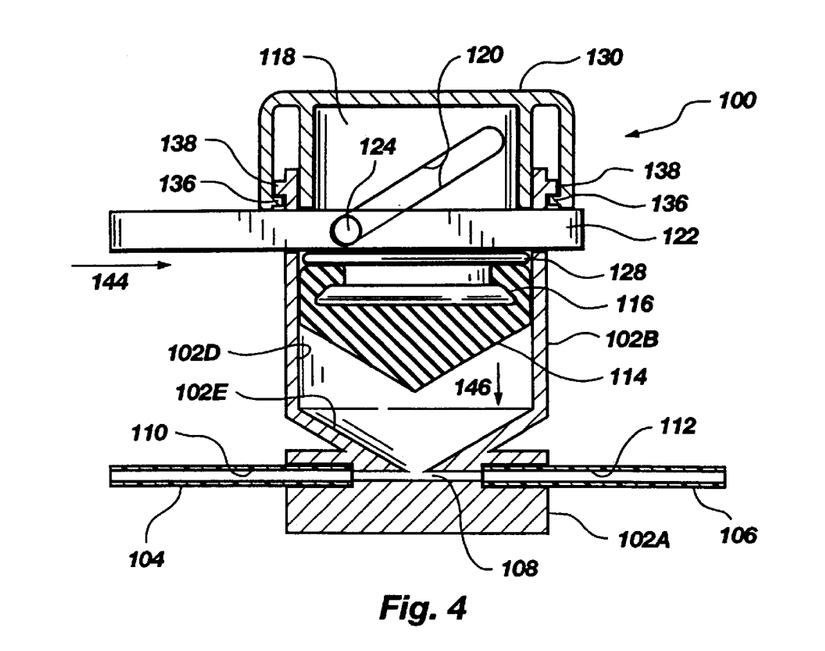
FIG. 4 is an elevational cross sectional view of the embodiment illustrated in FIG. 1 in a second operational position.

The cross sectional views of FIGS. 3 & 4 will be referred to next to further explain the structure of the blood sampling system 100 and the advantageous operation thereof. As seen in FIGS. 3 & 4, the cap 130 is provided with an inner rim 136 which engages a ridge 138 on the upper end of the body 102 to hold the cap 130 in place on the body 102. An inner lip 132 extends from the lower side of the cap 130 and forms a recess with an outer lip 134 into which the wall of the chamber housing 102B is received. The plunger tip 114, shown in cross section, makes a slidable, fluid-tight engagement with the interior wall 102D of the body 102. The plunger tip 114 is held in place on the plunger 128 by a retaining ring 116.

The blood sampling system 100 is represented in its normal position in FIG. 3. In the normal position, a substantially uninterrupted passageway 108 is formed between tube 104 and 106. In the normal position, normal fluid communication occurs between the patient (connected to tube 104) and the medical apparatus, such as a pressure transducer or intravenous fluid pump (connected to tube 106) as if the blood sampling system 100 was not present. Furthermore, the embodiments of the present invention avoids the problems which occur when the blood/fluid mixture is required to negotiate sharp bends or a long supplementary fluid path. Moreover, when in the normal position, the embodiments of the present invention described do not dampen the frequency response discerned by any pressure transducer being used.

Figure 5:
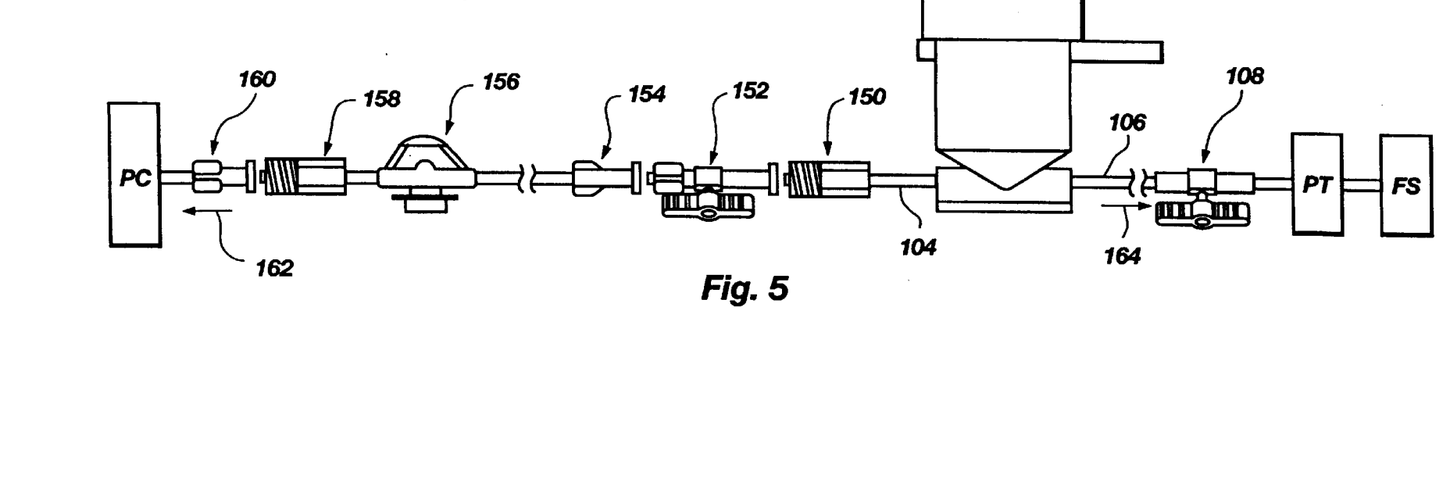
FIG. 5 is a diagrammatic representation of the embodiment of the present invention including a needleless blood sampling site and other fluid infusion structures.

As known in the art, in order to obtain a blood sample, the tube 106 is blocked (for example clamped or stopped) and a vacuum is created to aspirate the fluid contained in the tube 104 into the body 102 causing the patient's blood to be drawn up into the tube 104 so that unadulterated blood reaches a sampling site. FIG. 5 provides a schematic diagram of the blood sampling system of the present invention which is connected to a stop cock 152 and a needleless blood sampling device 156 which functions as a sampling site. Optionally, in accordance with the present invention, the tube 106 may be left open (rather than being, clamped or stopped) and satisfactory aspiration of blood will occur. The needleless blood sampling device 156 works in cooperation with a sample container (not represented in FIG. 5), generally in the form of a syringe which can be readily attached and remove and which is configured to withdraw a blood sample from the needleless blood sampling device 156. In practice, the blood sampling system must provide unadulterated blood at the position of the needleless blood sampling device 156. That is, the blood must not be substantially mixed with any infused fluid or other fluid which may otherwise normally be present in the tube 104.

Referring now to FIG. 3, to obtain a blood sample, a practitioner pushes the actuator in the direction of arrow 140. As the actuator is moved in the direction of arrow 140, the rod 124 is also moved. Since the combination of the plunger 116 and the fin 118 are held captive by the chamber housing 102B, the actuator slot 126, and the fin guide 131, as the rod 124 moves within the inclined slot 120 in the direction of arrow 140, the plunger 116 and the plunger tip 114 is moved upward in the direction of arrow 142 creating a chamber in communication with the passageway 108 as represented in FIG. 4.

As the actuator is moved by the medical practitioner, the structures described herein provide a suitable resistance to the pressure exerted by the medical practitioner. Such resistance provides the medical practitioner with a desirable feel and sensation when operating the blood sampling system and allows the practitioner to accurately control the rate at which the actuator 122 is moved. Moreover, as one end of the actuator 122 is pushed by the practitioner, the other end of the actuator 122 extends further from the body 102. In this way, the practitioner gains further control over the operation of the blood sampling system 100 by placing one portion of the practitioner's hand (e.g., a palm) on one end of the actuator 122 and another portion of the practitioner's hand (e.g., a middle finger) on the other end of the actuator.

The described structures of the blood sampling system also provides that the plunger substantially remains in whatever position it is found at when the practitioner ceases to push on the actuator 122. Thus, advantageously, there is no need for an additional locking mechanism to lock the plunger in its normal position, or in any other position. Moreover, the volume of the chamber created when the plunger is in the position represented in FIG. 4 is great enough to accommodate enough blood and other fluid mixture so that the blood which is drawn up from the patient's blood vessel to the sampling site (the needleless blood sampling device 156 in FIG. 5) is substantially unadulterated. For example, the volume of the aspiration chamber of the embodiments described herein can be at least 10 cc for applications involving adults and at least 1 cc for applications involving neonates. Other volumes can also be used within the scope of the present invention.

Referring again to FIG. 4, once the blood sample has been obtained, the practitioner pushes the actuator 122 in the direction of arrow 144 which causes the plunger 116 and the plunger tip 114 to move in the direction of arrow 146. Advantageously, the movement to expel is merely the reverse of the convenient movement to aspirate and the movement has the same desirable characteristics in both directions. The movement of the plunger 116 expels the contents of the chamber back into the passageway 108 and the plunger assumes its previous position illustrated in FIG. 3. The blood sampling system 100 functions reliably for one hundred or more aspiration and expulsion cycles.

It will be appreciated that the mating relationship between the bottom of the plunger tip 114 and the conical surface 102E of the chamber should be selected so that the contents of the chamber are expelled as completely as possible. While complete expulsion of the contents may not be practical in all circumstances, the residue which remains should be minimized so that clotting and other difficulties are minimized. When fabricating the conical surface 102E and the plunger tip 114 considerations such as the material and hardness of the plunger tip 114, matching or mismatching of the angles of the conical surface 102E and the surface of the plunger tip 114, and the thickness of the plunger tip 114 material, should all be considered. It is within the scope of the present invention to fabricate the angle of the conical surface 102E and the angle of the plunger tip surface 114 so that the angles substantially match, so that the angles are substantially different, and so that the angles vary along their surfaces.

As can be seen best in FIG. 4, the embodiments of the present invention advantageously minimizes the possibility of contamination of the patient's blood and infused fluids with contaminants from the surrounding environment. Desirably, the wetted surfaces of the blood sampling system cannot come into contact with the medical practitioner during use. Airborne contamination is also minimized since air flow into the chamber is restricted and any airborne contaminants which are deposited on the inner wall of the body 102D are wiped by the plunger tip 114. It is also within the scope of the present invention to utilize a flexible covering over one or more portions of the blood sampling system 100 to completely isolate the wetted surfaces from airborne contaminants.

FIG. 5 provides a schematic representation of an embodiment of the present invention with additional exemplary components which are commonly used in patient care applications. A blood sampling device 300 is represented with the tube 106 leading in the direction of arrow 164 to, for example, a pressure transducer PT and an infusion device acting as a fluid source FS. A clamp or stop cock structure 208 is preferably provided along the tube 106 for imposition during aspiration of blood. As mentioned earlier, by proper selection of the components shown in FIG. 5, and their relative positions, the stop cock 208 structure need not be operated during the sampling of blood. A tube 104 leads to a fitting 150 to which a stop cock 152 is preferably attached.

A needleless blood sampling port 156 is provided with fittings 154 and 158. The needleless blood sampling port 156 is preferably one available in the art from Migada, Inc. under the trademark LAB-SITE but other structures can also be used as a sampling site. A fitting 160 connects to tubing which leads to the patient in the direction of arrow 162. It is to be understood that many additional and/or alternative structures can also be included in embodiments of the present invention.

Figure 6:
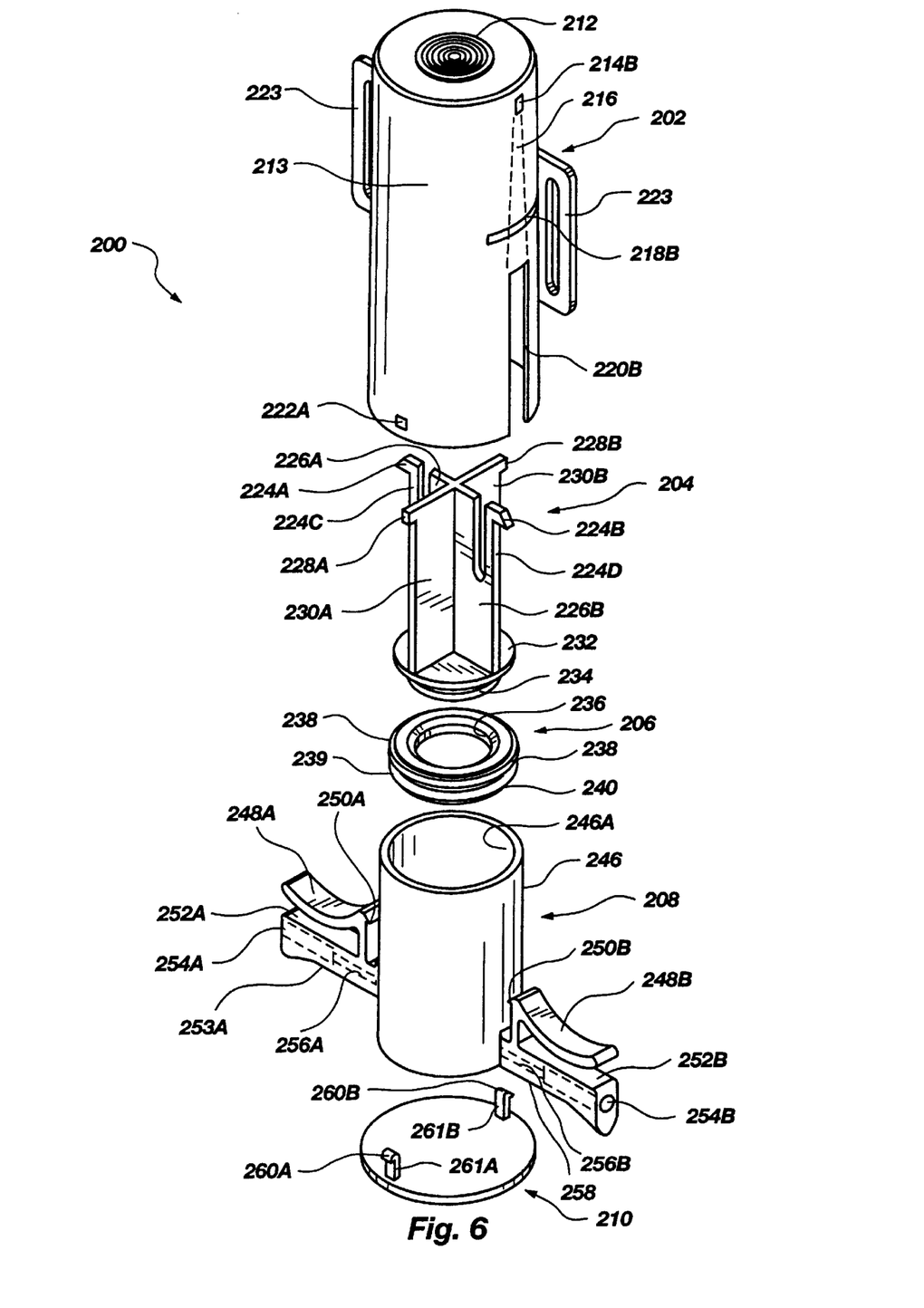
FIG. 6 is an exploded perspective view of a second presently preferred embodiment of the present invention.

Reference will next be made to FIGS. 6–9 to describe the structure and operation of a second presently preferred embodiment of the present invention. FIG. 6 will be referred to next to provide an overall description of the structure and operation of the second presently preferred embodiment of the present invention generally indicated at 200.

FIG. 6 is an exploded perspective view of the second presently preferred embodiment 200 illustrating the components thereof ready to be assembled. Illustrated in FIG. 6 is a shroud generally represented at 202. A plunger is also generally represented in FIG. 6 at 204 with a plunger tip being generally represented at 206 in FIG. 6. A body, generally represented at 208, and an end cap, generally represented at 210, are also illustrated in FIG. 6. Further information regarding the structure, assembly, and the operation of these components will be provided hereafter.

As explained earlier, the rigid components of the preferred embodiments are preferably fabricated from a clear plastic material suitable for medical applications. Desirably, the pertinent components are substantially visually transparent so that bubbles, clots, and other abnormalities within the fluid can be observed by a medical practitioner.

Figure 7:
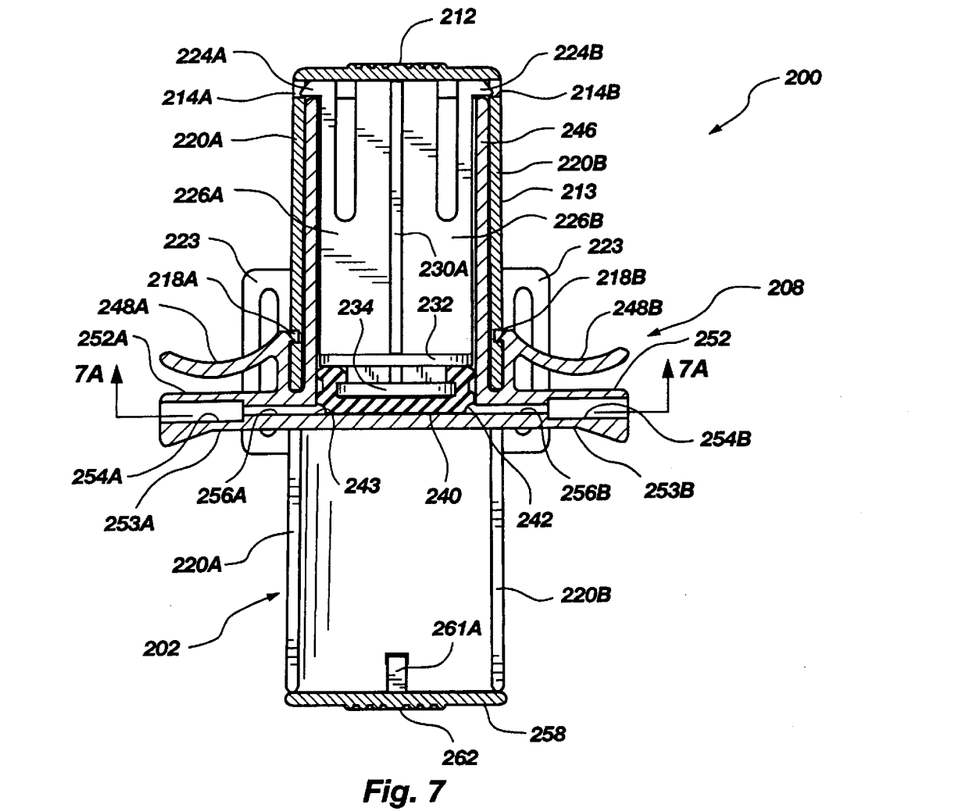
FIG. 7 is an elevational cross sectional view of the embodiment illustrated in FIG. 6 in a first operational position.
Figure 8:
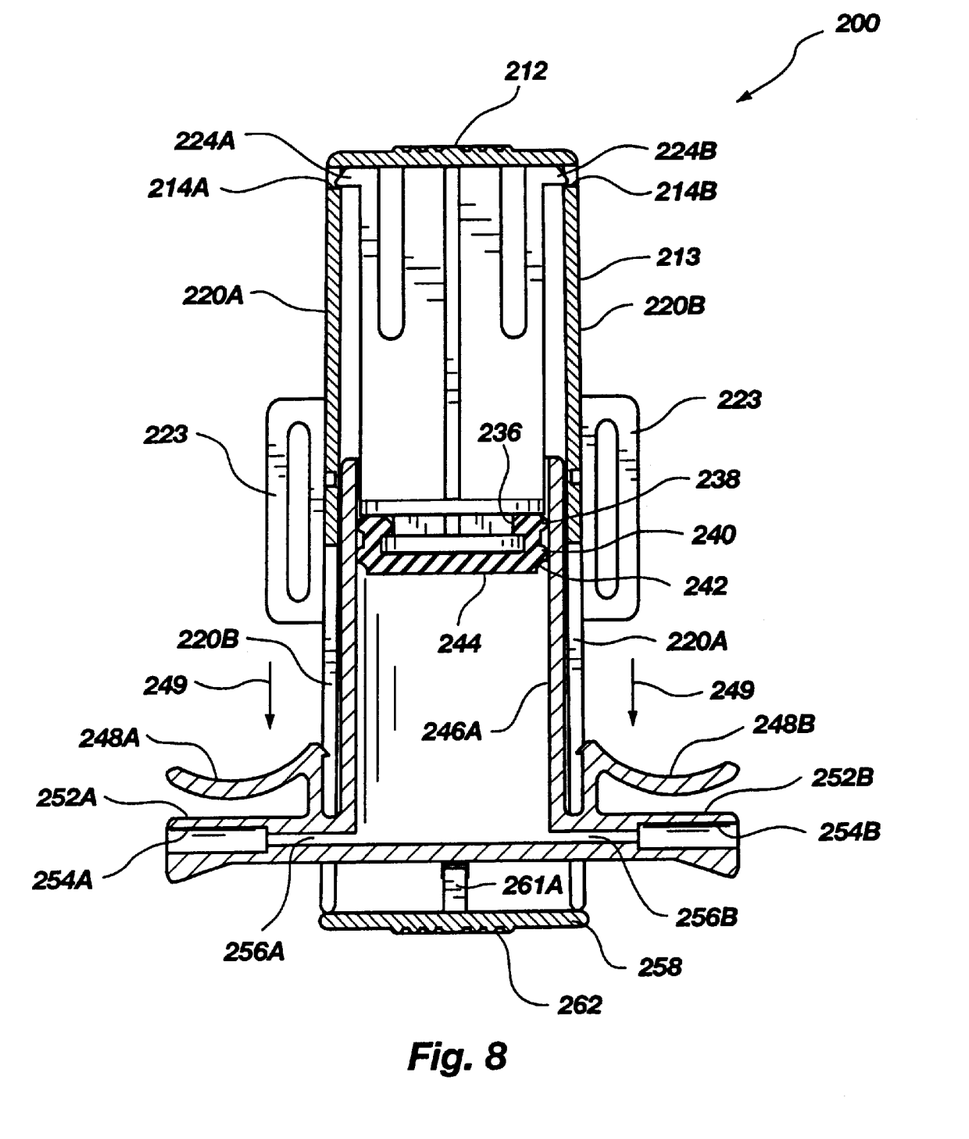
FIG. 8 is an elevational cross sectional view of the embodiment illustrated in FIG. 6 in a second operational position.

The shroud 202 preferably comprises a cylindrical receptacle 213. It will be appreciated that the shroud 202 functions as a housing for the plunger 204 and the body 208. Advantageously, as will be further explained shortly, the linear motion of the body 208 is limited to the length of the shroud 202. A concentric circle knoll 212 is preferably molded into the closed end of the shroud 202 as an indication to the medical practitioner where to place a thumb, finger, or palm during operation. An opening 214B is one of two openings (opening 214A is represented in FIGS. 7 and 8) which receive prongs 224A&B on the plunger 204. During assembly of the apparatus, it is preferred that the prongs 224A&B travel up tapered grooves, one of which is represented at 216, formed on the interior of the cylindrical receptacle 213 until the prongs 224A&B are received into their respective openings 214A&B. The plunger 204 is thus held in place in the interior of the cylindrical receptacle 213.

Also provided in the cylindrical receptacle 213 are two slots 218A (illustrated in FIG. 7 & 218B) which receive the teeth 250AB, respectively, in a locking engagement as will be explained further shortly. Also included in the cylindrical receptacle 213 are two cutouts, one shown in the perspective view of FIG. 6 at 220B and another at 220A in the cross sectional views of FIGS. 7 and 8. The cutouts 220A&B are dimensioned to receive the arms 252A&B included in the body 208 in a slidable fashion as will be explained in greater detail shortly.

Also illustrated in FIG. 6 is an opening 222A. The opening 222A is one of two openings which receive the prongs 260A&B on the end cap 210 thus holding the end cap 210 in place on the shroud 202. A slotted plate 223 is provided on the cylindrical receptacle 213. The slotted plate 223 is used to attach the apparatus 200 to the patient via a strap (not illustrated in the figures) or to another structure.

The plunger 204 fits within the cylindrical receptacle 213 of the shroud 202. The diameter of a cylindrical base 232 is selected so that when the plunger 204 is held within the cylindrical receptacle 213 a gap exists between the circumference of the cylindrical base 232 and the interior of the cylindrical receptacle 213. The gap is best seen in the cross sectional views of FIG. 8 and is provided to receive a cylindrical vessel 246 included in the body 208.

As shown best in FIG. 6, four legs 226A&B and 230A&B extend perpendicularly from the cylindrical base 232 with each of the legs 226A&B and 230A&B preferably being oriented at right angles to each other. The legs 226A&B are provided with the two prongs 224A&B on the end of tines 224C&D which flex and allow prongs 224A&B to move as the plunger 204 is inserted into the cylindrical body 213 and engage the openings 214A&B. The legs 230A&B are each provided with a post 228A&B. The posts 228A&B each engage the interior surface of the cylindrical receptacle 213. The posts 228A&B function to further hold the plunger 204 in place and maintain the gap between the legs 226A&B and 230A&B and the interior of the cylindrical receptacle 213. A retaining disc 234 is provided on the plunger 204 to hold a plunger tip 206 in place thereon.

The plunger tip 206 is preferably fabricated from a resilient material, for example those materials from which syringe plunger tips are fabricated in the industry. A groove 236 is provided on the interior of the plunger tip 206 into which the retaining disc 234 is received. As seen best in the cross sectional views of FIGS. 7 and 8, the groove 236 and retaining disc 234 hold the plunger tip 206 against the base 232. Also as seen best in FIGS. 7 and 8, the plunger tip 206 is provided with a first wiper 239 and a second wiper 238 which are particularly configured to slidably engage the interior surface 246A of the cylindrical vessel 246. The function of the plunger tip 206 will be further discussed later.

Figure 9:
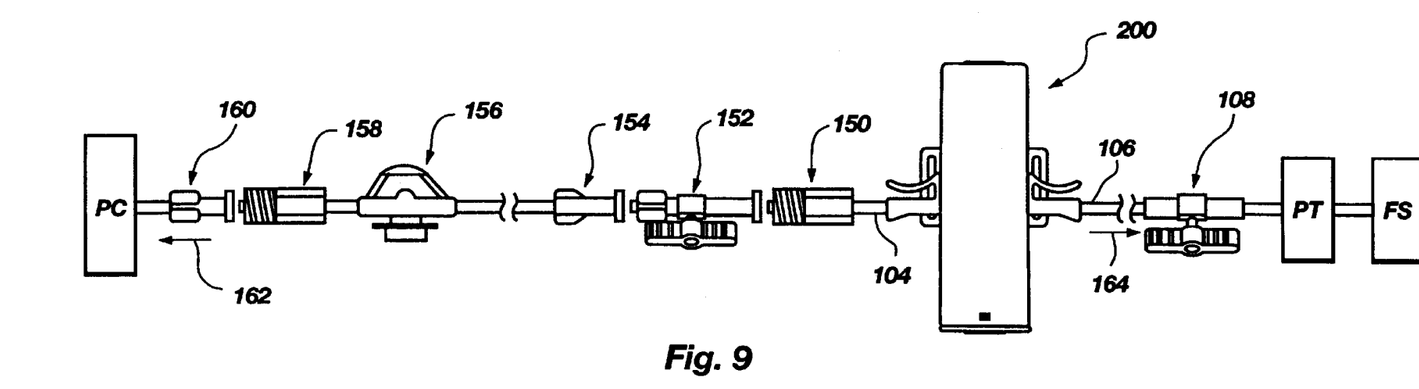
FIG. 9 is a diagrammatic representation of the second embodiment of the present invention including a needleless blood sampling site and other fluid infusion structures.

Referring again to FIG. 6, the body 208 includes the cylindrical vessel 246 and perpendicularly extending arms 252A&B. The arms 252A&B can preferably be molded as part of the cylindrical vessel 246. Each of the arms 252A&B includes passageways 256A&B, respectively, each of which communicate with the interior of the cylindrical vessel 246 as seen best in the cross sectional view of FIGS. 7 and 8. At the ends of each of the passageways 256A&B are tubing bores 254A&B, respectively, which receive tubing segments 204 and 206, respectively, as represented in FIG. 9. The tubing segments 204 and 206 are preferably lengths of clear tubing generally used in medical applications and are secured to the tubing bores 254A&B in a manner known in the art.

As shown best in FIG. 6, a pair of finger grips 248A&B are each flexibly attached to the arms 252A&B, respectively.

The flexible attachment of the finger grips 248A&B to the arms 252A&B (1) allows the teeth to lockingly engage the slots 218A&B when the arms are slid up to the closed ends of cutouts 220A&B thus locking the shroud 202 and the body 208 in a fixed position relative to each other and (2) allows the user to release the teeth 250A&B from the slots 218A&B allowing the shroud 202 and the body 208 to move with respect to each other.

As will be further discussed in connection with FIGS. 7 and 8, when the second embodiment of the present invention 200 is assembled the plunger 204 with the plunger tip 206 are held in the shroud 202 with the body 208 also being inserted into the shroud 202 with the plunger 204 and the plunger tip 206 being held captive within the interior of the cylindrical vessel 246. To hold all of these components together in their proper relationship, an end cap 210 is locked into the open end of the shroud 202. The end cap 210 includes a plate 258 from which a pair of posts 261A&B perpendicularly extend. Each of the posts 261A&B are provided with claws 260A&B (see FIG. 6), respectively, which engage openings, one of which is represented at 222A, provided in the shroud 202. Once assembled, the second embodiment can advantageously be utilized to aspirate and expel fluids as will next be explained.

Figure 7A:
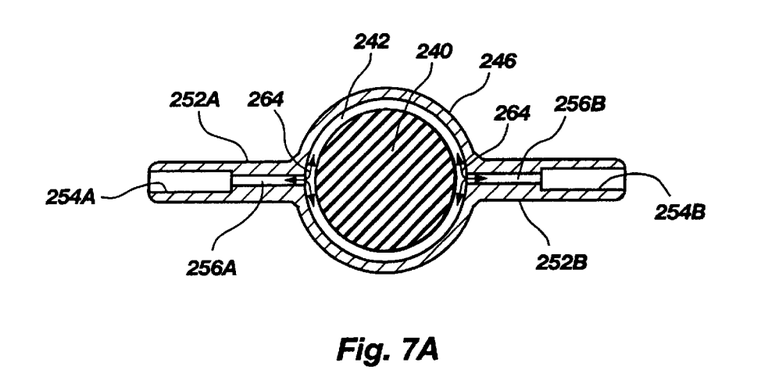
FIG. 7A is a cross sectional view taken along line 7A—7A of FIG. 7.

Reference with next be made to FIG. 7 which is an elevational cross sectional view of the embodiment illustrated in FIG. 6 in a first operational position. In the first operational position all of the fluid has been expelled from the second embodiment 200 and a fluid path has been created between the tubing bore 254A and the tubing bore 254B. The first operational position is also referred to as the normal position since it is normal for substantially all of the fluid to be expelled from the device except for the fluid which will be described shortly in connection with FIG. 7A.

In the cross sectional view of FIG. 7, the relationship between the shroud 202 and the body 208 can be observed. In the first operational position illustrated in FIG. 7, the cylindrical vessel 246 of the body 208 has been pushed as far as possible into the closed end of the shroud 202 towards the concentric circle knoll 212. As can be readily observed in FIG. 7, the cylindrical vessel 246 has a diameter which closely fits within the interior of the cylindrical receptacle 213 of the shroud 202.

In order to move the body 208 into the first operational position shown in FIG. 7, the user preferably places the first end of the shroud 202 having the concentric circle knoll 212 against the thumb or palm of a hand. The user also places a finger on a first finger rest 253A (located on one side of the arm 252A) and another finger on a second finger rest 253B (located on one side of the arm 252B). With the first end of the shroud positioned against the user's palm or against the user's thumb, and a finger positioned on each of the finger rests 253A&B, the user can utilize a flexion motion of the fingers and/or the thumb (movement of the fingers and thumb toward the palm) to move the body 208 against the first end of the shroud 202 to the position represented in FIG. 7.

As seen best in the cross sectional view of FIG. 7, the prongs 224A&B have been received into the openings 214A&B, respectively, holding the plunger 204 in the shroud 208. The legs 226A&B which support the prongs 224A&B are dimensioned such that the plunger fits within the cylindrical vessel 246 as the body 208 moves within the shroud 202. It will be appreciated that the body 208 and the plunger 204 together form a chamber and are one preferred arrangement for selectively increasing and decreasing the volume or size of the chamber which is formed.

As the body moves to the position represented in FIG. 7, the volume of the chamber volume created by the wall of the cylindrical vessel 246 and the first wiper 238 of the plunger 206 is reduced to nearly zero and the fluid contained in the body is expelled through passageways 256A&B. A flat end 240 provided on the plunger tip 206 makes contact with the floor 243 of the body 202. As shown in the cross sectional view of FIG. 7A (taken along line 7A—7A of FIG. 7), substantially all of the fluid is squeezed out in the area where contact is made between the flat end 240 of the plunger tip 206 and the floor 243 of the body 208. Importantly, a fluid channel 242 remains to provide a fluid path in the directions of arrows 264 and between the passageway 256A and passageway 256B. Significantly, using the arrangement represented in the drawing, there is no backspace where blood can accumulate and coagulate, as with previously available devices, when the apparatus is placed in its normal position.

The fluid channel 242 is configured to allow fluid flow through the channel 242 as well as allowing pressure pulses to be transmitted through the channel 242. FIG. 9 provides a diagrammatic representation of the second embodiment 200 of the present invention including the needleless blood sampling site 156, the patient catheter PC, the pressure transducer PT, and the fluid source FS. The fluid channel 242 (FIG. 7A) must provide suitable fluid flow from the fluid source (FS in FIG. 9) and must accurately transmit pressure pulses from the patient catheter (PC in FIG. 9) to the pressure transducer (PT in FIG. 9).

The fluid channel 242 is configured to provide a continuous fluid column therethrough by minimizing obstructions, reducing the formation of gas bubbles, and providing the proper volume of fluid, within the fluid channel 242 for accurate transmission of pressure pulses therethrough. The configuration of the fluid channel 242 is such that the formation of clots therein is minimized. The formation of clots within the fluid channel 242 blocks the desirable flow of fluid therethrough and degrades the transmission of pressure pulses therethrough. The configuration of the fluid path 264 provides a smooth transition between the tubes (204 and 206 in FIG. 9) connected to the tubing bores 254A&B so as to minimize the formation of clots and accurately transmit pressure pulses to the pressure transducer (PT in FIG. 9). Those skilled in the art will appreciate that the materials for the body 208 and the plunger tip 206 should be selected from those available in the industry to achieve the enumerated benefits among other desirable characteristics discussed herein.

Reference will next be made to FIG. 8. FIG. 8 is a elevational cross sectional view of the second presently preferred embodiment of the present invention in a second operational position. When moved to the second operational position in the direction indicated by arrows 249, fluid is aspirated into the cylindrical vessel 246 of the body 208. In the arrangement represented in FIG. 9, moving to the second operational position causes the fluid to be drawn up from the patient catheter PC to the blood sampling site 156 such that blood, or other bodily fluid, can be withdrawn into a sample container (not represented in the figures).

In order to move to the body 208 in the direction of arrows 249 to the second operational position represented in FIG. 8, the user preferably places the second end of the shroud 202 having the concentric circle knoll 262 against the thumb of one hand. The user also preferably places one finger (for example a middle finger) on the finger grip 248A and another finger (for example a ring finger) on the finger grip 249B. With the second end of the shroud 202 and the concentric circle knoll 262 positioned against the user's thumb and with a finger positioned on each of the finger grips 248A&B, the user utilizes a pulling motion to flex the finger grips 248A&B to release the teeth 250A&B from the slots 218A&B, respectively, as shown best in FIG. 7.

The finger grips 248A&B are biased so that they engage the slots 218A&B and lock the body 202 in its normal position illustrated in FIG. 7. Importantly, the device 200 will remain in the normal position most of the time during use and the finger grip 248A&B with teeth 250A&B engaging the slots 218A&B ensures that the device 200 will remain in the normal position even though the device 200 is inadvertently bumped by the patient or practitioner or even if the highest expected pressure is introduced in the fluid channel. Remaining in the normal position is important to the convenient and safe operation of the device 200.

With the user's fingers preferably positioned as described, the user pulls in the direction of arrows 249. The pulling action, which desirably is the same action as is used to move the device 200 to its normal position but applied to the opposite end of the device, causes the first wiper 240 and the second wiper 238 to slide along the interior surface 246A of the cylindrical vessel 246 of the body 208. The fluid tight seal formed between the first wiper 240, the second wiper 238 and the inner wall 246A cause a vacuum to be developed in the chamber formed by the interior surface 246A of the cylindrical vessel 246 and the first wiper 238 of the plunger 206. The resulting vacuum causes fluid to be aspirated into the chamber formed in the body 208.

Figure 9A:
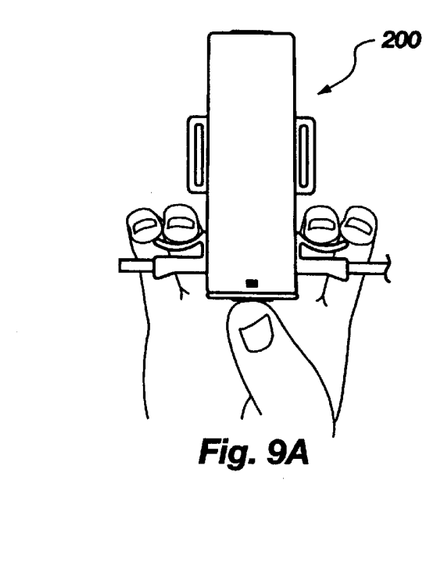
FIG. 9A is a diagrammatic representation of the second embodiment of the present invention being operated to withdraw a sample of blood.

Reference will next be made to FIG. 9 which is a diagrammatic representation of the second embodiment 200 shown in a normal position. In the normal operational position the flow of fluid occurs from the fluid source FS, through the pressure transducer PT and the apparatus 200 and the associated tubing and structure, to the patient catheter PC. When it is desired to obtain a blood sample, the practitioner can preferably grasp the apparatus 200 as illustrated in FIG. 9A. Using two fingers and the thumb of one hand, the body (hidden within the apparatus 200 in the view of FIG. 9) is moved to the sampling position shown in FIG. 9A and fluid is aspirated into the chamber formed in the body.

In view of the forgoing, it will be appreciated that the present invention provides a patient fluid sampling system which is compact and convenient to operate and which can aspirate blood up to a sampling site with the medical practitioner using not more than one hand. The present invention also provides an in-line blood sampling system which is reliable and inexpensive to manufacture, which minimizes the risk of infection due to operation thereof, and which provides a blood sampling system which provides appropriate resistance and feel for the medical practitioner using the system.

These benefits of the present invention are in contrast to the disadvantages of the previously available devices which require two hands to operate or require awkward motions by the practitioner. The present invention allows sufficiently large volumes to be aspirated while maintaining the apparatus in a small and convenient size. The present invention also avoids contamination of the fluid and allows the practitioner to use the same motion to return the apparatus to the normal position as was used to aspirate fluid. Moreover, the fluid path created when the apparatus is in its normal position avoids the formation of clots which would otherwise dampen the pressure waves to the pressure transducer (PT in FIG. 9) or the flow of fluid to the patient catheter (PC in FIG. 9). These and other advantages provide a blood sampling system which is more efficient and reliable than those previously available.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for sampling a body fluid through a tube attached to a patient's body, the system being operable by a user having a hand including a palm, a thumb and at least a first finger and a second finger, the system comprising:
   a fluid sampling site connected to the tube;
   means for receiving the tube;
   means for forming a chamber; and
   means for selectively increasing the size of the chamber to a maximum volume and for decreasing the size of the chamber to a minimum volume, the means for increasing and decreasing the size of the chamber being operable by moving the first and second fingers or the thumb in a flexion movement toward the palm to achieve the maximum volume of the chamber, the means for increasing and decreasing the size of the chamber also being operable by moving the first and second fingers or the thumb in a flexion movement toward the palm to achieve the minimum volume of the chamber such that the same motion of the user's first and second fingers can selectively accomplish the maximum volume to aspirate fluid from the patient's body to the fluid sampling site or accomplish the minimum volume to expel the fluid into the patient's body.

2. A system as defined in claim 1 further comprising shroud means for covering the means for selectively increasing and decreasing the size of the chamber, the shroud means having a length and the length not changing as the minimum volume and the maximum volume is achieved.

3. A system as defined in claim 1 wherein the means for forming a chamber comprises a substantially cylindrically shaped body.

4. A system as defined in claim 3 wherein the means for selectively increasing the size of the chamber comprises;
   a shroud at least substantially covering the body; and
   a plunger attached to one end of the shroud, the plunger being slidably inserted into the body.

5. A system as defined in claim 3 wherein the body comprises a substantially clear plastic material.

6. A system as defined in claim 3 wherein the body comprises a substantially flat bottom and wherein the plunger comprises a tip form from a resilient material, the tip having a flat surface which mates against the flat bottom when the volume of the chamber is minimized, the tip also comprising a fluid channel formed therein.

7. A system as defined in claim 6 wherein fluid channel comprises a circular channel formed in about the perimeter of the tip.

8. A system for sampling a body fluid through a tube attached to a patient's body, the system being operable by a user having a hand including a palm, a thumb and at least a first finger and a second finger, the system comprising:
   a fluid sampling site connected to the tube;

means for receiving the tube;
means for forming a chamber;
means for housing the means for forming a chamber; and
means for selectively increasing and decreasing the size of the chamber, the means for increasing and decreasing the size of the chamber being positioned within the means for housing and including means for receiving the first finger and the second finger extending out of the means for housing, the size of the chamber being altered as the means for receiving the first finger and the second finger being linearly moved along the length of the of the means for housing.

9. A system for sampling a body fluid as defined in claim 8 wherein:
the means for housing comprises a shroud and
wherein the means for forming a chamber comprises a body and a plunger;
wherein the means for selectively increasing and decreasing comprises slots formed within the shroud wherein the means for receiving the first finger and the second finger are slidably received and wherein the means for receiving the first finger and the second finger are attached to the body.

10. A system for sampling a body fluid as defined in claim 8 wherein the chamber has a volume of at least ten cubic centimeters.

11. A system as for sampling a body fluid as defined in claim 8 wherein the sampling site comprises a needleless sampling site.

12. A system as for sampling a body fluid as defined in claim 8 wherein the length of the housing means is not greater than six inches.

13. A system as for sampling a body fluid as defined in claim 8 wherein the length of the housing means is not greater than four inches.

14. A system as for sampling a body fluid as defined in claim 8 further comprising:
means for receiving fluid from a fluid source; and
means for forming a fluid path through the chamber from the means for receiving the tube to the means for receiving fluid when the size of the chamber is minimized.

15. A system as for sampling a body fluid as defined in claim 9 wherein the plunger comprises a flat tip.

16. A system for sampling a body fluid through a conduit attached to a patient's body, the system comprising:
a sampling site connected to the conduit, the conduit leading to a vessel in the patient's body;
means for releasably receiving the conduit;
means for forming a chamber;
means for connecting the chamber to the conduit such that fluid can be interchanged between the conduit and the chamber;
plunger means for drawing the fluid from the conduit into the chamber and for expelling the fluid from the chamber into the conduit;
actuator means for actuating the plunger means, the means for actuating the plunger means comprising:
means, extending outwardly from the chamber, for receiving a portion of a user's hand; and
means for translating a force applied by the user's hand in a direction substantially perpendicular to the chamber into movement of the plunger means such that fluid is selectively drawn into and expelled from the chamber.

17. A system as defined in claim 16 wherein the means for translating comprises:
a slot connected to the plunger means and oriented at an angle with respect to the direction of travel of the plunger; and
a rod connected to the actuator means and slidably positioned in the slot.

18. A system as defined in claim 16 wherein the sampling site comprises a needleless sampling port.

19. A system as defined in claim 16 wherein the means for forming a chamber comprises a substantially cylindrically shaped body.

20. A system as defined in claim 19 wherein the body comprises a substantially clear plastic material.

21. A system as defined in claim 19 wherein the actuator means comprises a linearly shaped actuator and the body comprises first and second openings through which the actuator passes substantially perpendicularly to the direction of travel of the plunger means.

22. A system as defined in claim 16 wherein the plunger means comprises a resilient material formed in a first conical shape and wherein the means for forming a chamber comprises a bottom, the bottom having a second conical shape and an aperture at the apex of the conical shape, the aperture providing fluid communication with the conduit. bottom, the bottom having a second conical shape and an aperture at the apex of the conical shape, the aperture providing fluid communication with the tube.

23. A system as defined in claim 16 wherein the means for forming a chamber comprises a cap covering the chamber.

24. A system for sampling a patient's internal fluid through a conduit connected to a patient, the system comprising:
a chamber in fluid communication with the conduit, the chamber having an inner wall;
a body holding the chamber, the body having an external side wall;
a plunger slidably positioned in the chamber and in contact with the inner wall;
an actuator having first and second ends, the actuator passing through the body and having a first position wherein at least the first end of the actuator extends from the body and a second position wherein at least the second end of the actuator extends from the body such that a user's hand can apply pressure to the actuator when in its first position and in its second position such that the user can move the actuator from the first position to the second position;
means for translating the movement of the actuator between the first position and the second position into movement of the plunger between a first position which decreases the volume of the chamber and a second position which increases the volume of the chamber such that movement of the actuator from the first position to the second position causes fluid to be drawn into the chamber and movement of the actuator from the second position to the first position causes fluid to be expelled from the chamber; and
a sampling site connected to the conduit between the patient and the chamber, the patient's fluid being drawn from the vessel to the sampling site as the plunger moves between its first position and its second position such that a sample can be withdrawn at the sampling site.

25. A system as defined in claim 24 wherein the means for translating comprises:

a slot connected to the plunger and oriented at an angle with respect to the direction of travel of the plunger; and a rod connected to the actuator and slidably positioned in the groove.

26. A system as defined in claim 24 wherein the sampling site comprises a needleless sampling port.

27. A system as defined in claim 24 wherein the body comprises a substantially cylindrically shaped body.

28. A system as defined in claim 24 wherein the body comprises a substantially clear plastic material.

29. A system as defined in claim 24 wherein the actuator is linearly shaped and the body includes first and second openings through which the actuator passes.

30. A system as defined in claim 24 wherein the plunger comprises a resilient material formed in a first conical shape, the chamber having a bottom, the bottom having a second conical shape and an aperture at the apex of the conical shape, the aperture providing fluid communication with the conduit.

31. A system as defined in claim 30 wherein the angle of the first conical shape substantially matches the angle of the second conical shape.

32. A system as defined in claim 30 wherein the angle of the first conical shape is different than the angle of the second conical shape.

33. A system as defined in claim 30 wherein the angle of the first conical shape is greater than the angle of the second conical shape.

34. A system as defined in claim 24 further comprising:

a cap over the body; and means for guiding the plunger between the first position and the second position.

* * * * *